(12) United States Patent
Keall et al.

(10) Patent No.: US 7,955,270 B2
(45) Date of Patent: Jun. 7, 2011

(54) METHOD AND APPARATUS FOR RESPIRATORY AUDIO-VISUAL BIOFEEDBACK FOR IMAGING AND RADIOTHERAPY

(75) Inventors: Paul Keall, Stanford, CA (US); Rohini George, Richmond, VA (US); Radhe Mohan, Pearland, TX (US); Keith Miller, Fort Myers, FL (US); Theodore Chung, Richmond, VA (US)

(73) Assignee: Stanford University, Palo Alto, CA (US)

( * ) Notice: Subject to any disclaimer, the term of this patent is extended or adjusted under 35 U.S.C. 154(b) by 1250 days.

(21) Appl. No.: 11/538,548

(22) Filed: Oct. 4, 2006

(65) Prior Publication Data

US 2007/0093723 A1   Apr. 26, 2007

Related U.S. Application Data

(60) Provisional application No. 60/722,998, filed on Oct. 4, 2005.

(51) Int. Cl.
*A61B 5/08* (2006.01)

(52) U.S. Cl. ........................ 600/534; 600/411

(58) Field of Classification Search .................. 600/529, 600/533, 534, 538, 410, 411, 413, 418, 427, 600/428
See application file for complete search history.

(56) References Cited

U.S. PATENT DOCUMENTS

| 4,387,722 A * | 6/1983 | Kearns ........................ 600/529 |
| 5,067,494 A * | 11/1991 | Rienmueller et al. ........ 600/428 |
| 7,393,329 B1 * | 7/2008 | Wong et al. .................. 600/534 |
| 2006/0129044 A1 * | 6/2006 | Le Corre ..................... 600/428 |

FOREIGN PATENT DOCUMENTS

WO   WO2002085455   * 10/2002

* cited by examiner

*Primary Examiner* — Charles A Marmor, II
*Assistant Examiner* — Michael D'Angelo
(74) *Attorney, Agent, or Firm* — Whitham, Curtis, Christofferson & Cook, P.C.

(57) ABSTRACT

An improved method and apparatus for respiratory audio-visual biofeedback are disclosed. A guide patterned after a breathing cycle comfortable to the patient serves as a target. The target is displayed as a bar moving vertically upward during inhale and vertically downward during exhale, between fixed end ex-hale and end in-hale limits. The patient's current respiratory position is also displayed as a bar, oriented parallel to the target bar so that the difference between the current position and the target position is easy for the patient to see.

20 Claims, 2 Drawing Sheets

METHOD AND APPARATUS FOR RESPIRATORY AUDIO-VISUAL BIOFEEDBACK FOR IMAGING AND RADIOTHERAPY

This patent application claims priority from U.S. Provisional application 60/722,998 filed on Oct. 4, 2005, which is incorporated by reference herein.

FEDERALLY-SPONSORED RESEARCH OR DEVELOPMENT

This invention was made with Government support under contract CA093626 awarded by the National Institutes of Health. The Government has certain rights in this invention.

BACKGROUND OF THE INVENTION

1. Field of the Invention

The present invention generally relates to respiratory imaging techniques used in radiotherapy and, in particular, to techniques for using audio-visual biofeedback to improve accuracy.

2. Background Description

Respiratory motion creates several problems for thoracic radiology. It degrades anatomic position reproducibility during imaging. It necessitates larger margins during radiotherapy planning. And it causes errors during radiation delivery.

In a PHD thesis entitled "Investigating the impact of audio instruction and audio-visual biofeedback for lung cancer radiation therapy" (Virginia Commonwealth University, 2005), Rohini George describes a twenty-four patient study conducted at Virginia Commonwealth University. The study demonstrated the improvement in respiratory reproducibility and therefore image quality and radiotherapy treatment accuracy that can be obtained with audio-visual biofeedback. This study used the output of the Varian RPM (Real-time Position Management) respiratory gating system for the audio-visual biofeedback.

Operation of the Varian system is shown in FIG. 1. A patient 110 lies in a prone position, viewing a TV screen 120. The TV screen has a built-in speaker (not shown) used during the audio instructions and the audio-visual biofeedback. A marker block 130 is placed on the patient's abdomen between the umbilicus and the xyphoid, allowing measurement of the current position of the patient's breathing. In the Varian system, the image 122 presented to the patient 110 on screen 120 shows guides for the maximum 124 and minimum 126 extent of breathing, thereby allowing the patient to observe current position 128 in relation to these upper 124 and lower 126 limits. The respiratory signal 128 obtained is the anterior-posterior motion of the marker block 130.

SUMMARY OF THE INVENTION

It will be noted that the Varian system shows to the patient limiting guides for the maximum and minimum extent of breathing. These limits, coupled with biofeedback of the patient's current position, permit the patient to use the biofeedback to keep within these limits. However, there are no guides for the intermediate breathing states between end-inhale and end-exhale.

It is therefore an object of the present invention to provide a guide for the patient to use the biofeedback to track and conform to intermediate breathing states.

It is also an object of the invention to provide a guide that tracks intermediate states continuously between end ex-hale and end in-hale.

Yet another object of the invention is to provide a guide that displays the minimum necessary information to the patient, maximizing the patient's ability to follow the guide.

One aspect of the invention is a method, and another aspect is a display apparatus, for respiratory audio-visual biofeedback for imaging and radiotherapy treatment, in which a target measure of the patient's respiratory position is displayed, along with a current measure of the patient's respiratory position, the two measures being aligned in the display so that a difference between the patient's current respiratory position and the patient's target respiratory position is readily apparent to the patient.

Another aspect of the invention provides a marker along a line from an end-exhale position to an end-inhale position for measuring target and current positions, the lines for target respiratory position and current respiratory position being aligned in parallel in a first direction so that if the patient's current position is synchronized with the patient's target position the corresponding markers are aligned in a second direction perpendicular to the first direction. In a variation on this aspect, the corresponding markers are straight line segments in the second direction. In a further variation, each straight line segment is at one end of a bar extending along the first direction. In yet another variation, the bar measuring the patient's current respiratory position extends from the current line segment in the direction of the end-exhale position. Another variation provides for marking a target end-exhale limit and a target end in-hale limit on the display, as is done in the prior art. These limits may be marked by lines extending in the second direction. It is also an aspect of the invention to provide that the first direction is vertical and the second direction is horizontal, or vice versa, as the display is viewed by the patient.

In another aspect, the invention may be viewed as an improvement on prior art respiratory audio-visual biofeedback for imaging and radiotherapy treatment. The prior art displays for a patient target end ex-hale and target end in-hale limits together with a current respiratory position to be kept within these limits by control of breathing by the patient. The improvement provides for displaying a target respiratory position of the patient, the target position varying continuously in accordance with a pattern learned from the patient, and aligning the display of the target respiratory position and the display of the current respiratory position so that a difference between the patient's current respiratory position and the patient's target respiratory position is readily apparent to the patient. In a further aspect of the invention, the target position is determined by an average of respiratory traces obtained by monitoring the patient. The target position may also be determined, in another aspect of the invention, by a mathematical algorithm falling within an envelope established by a plurality of respiratory traces obtained by monitoring the patient.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The invention details a specific method of audiovisual biofeedback to improve the accuracy of diagnostic imaging and radiotherapy imaging and treatment by displaying the current respiratory position and the target position at any moment in time simultaneously. The target position corresponds to a respiration trace learned from a pattern that the patient is comfortable with, either an average breathing trace or a suitable mathematical curve approximating the pattern learned from the patient. The target position moves and serves as the guide for patient control of the patient's current respiratory position.

Figure 1:
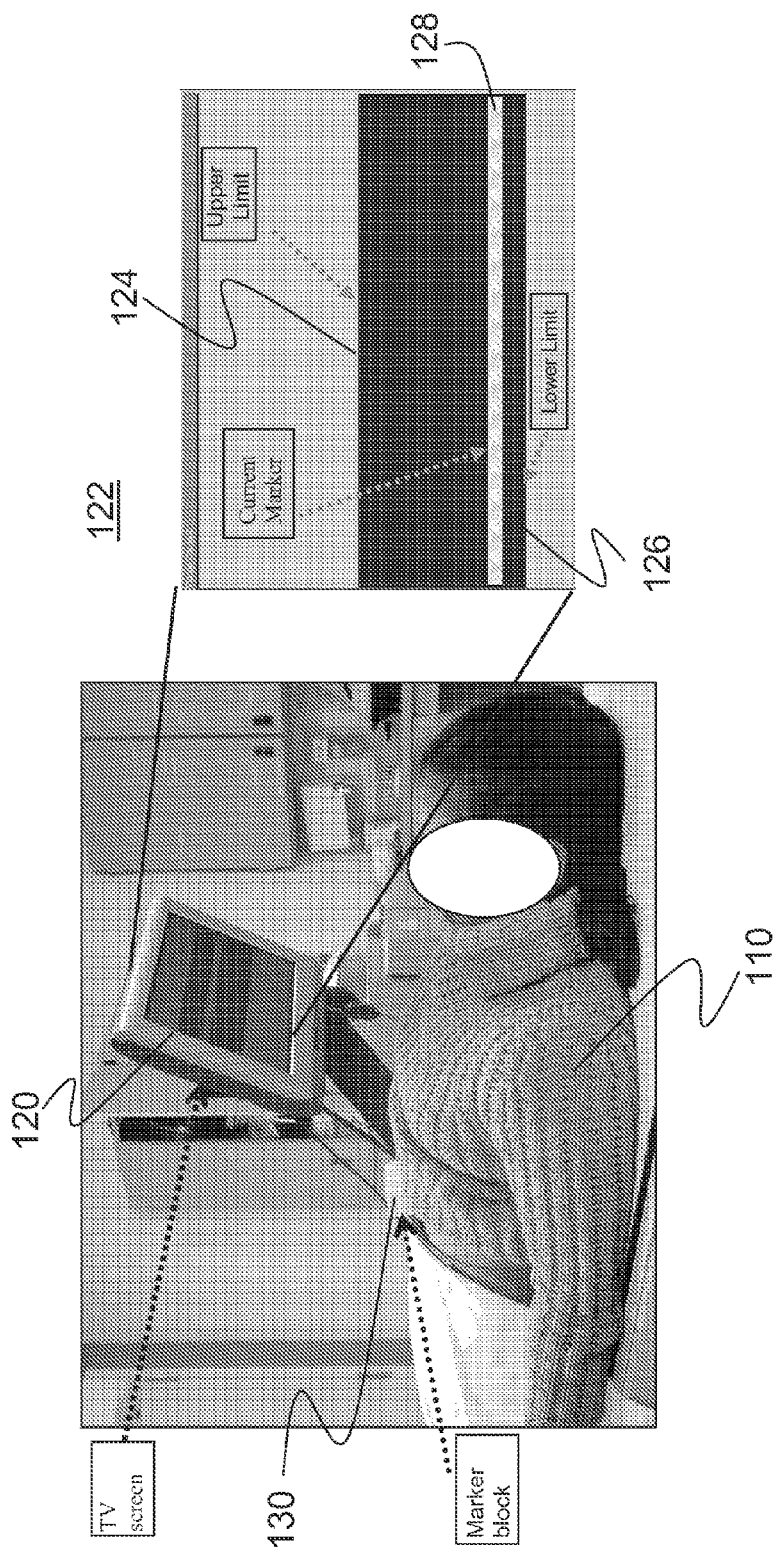
FIG. 1 shows a prior art setup for audio-visual biofeedback.
Figure 2:
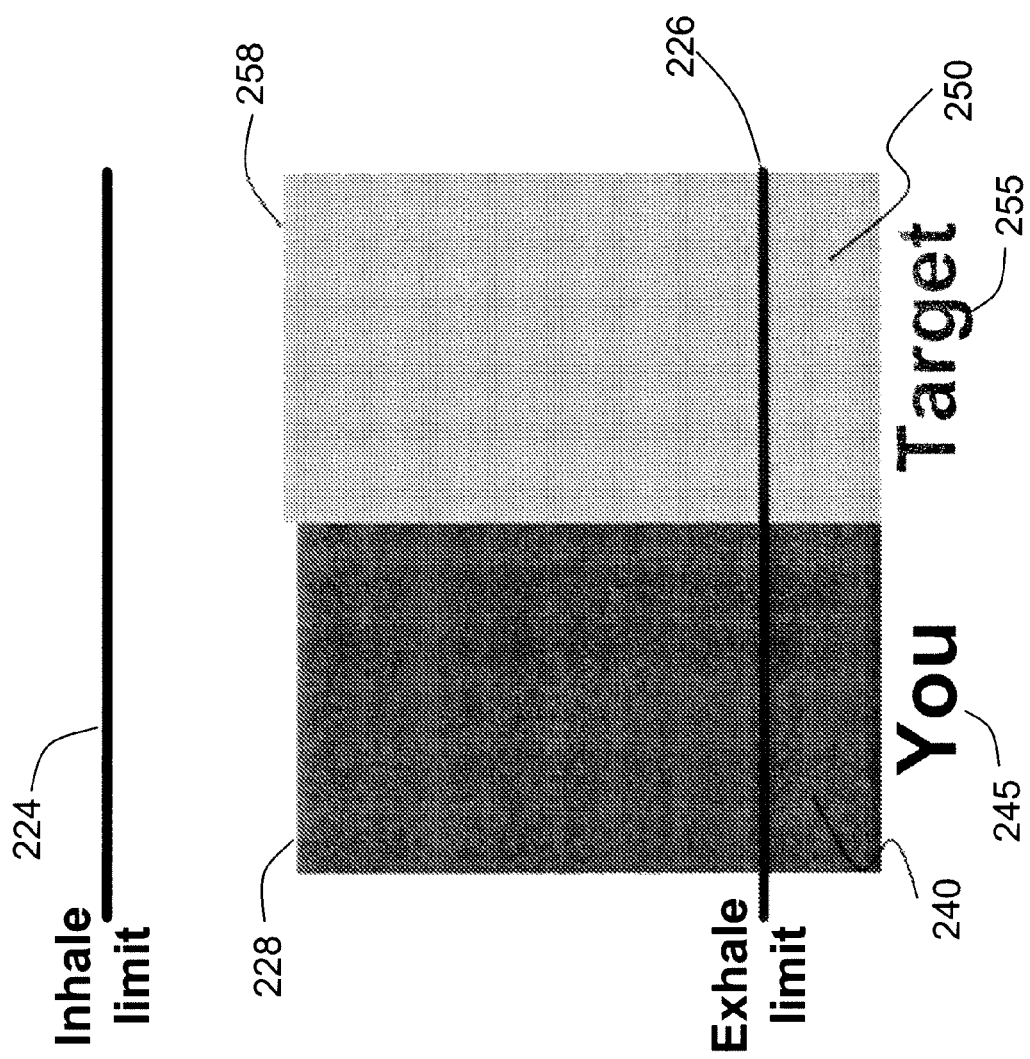
FIG. 2 is a schematic diagram of an improved audio-visual biofeedback display screen, showing improved guides.

A best mode of implementing the invention is shown in FIG. 2. The target respiratory position 258 is shown as the top horizontal edge of a bar 250. The top edge 258 moves vertically, in accordance with the pattern learned from the patient. As with the prior art system, an inhale limit 224 and an exhale limit 226 are shown on the display as upper and lower limit guides. The patient's current respiratory position 228 is shown as the top horizontal edge of a bar 240, moving vertically upward as the patient inhales and vertically downward as the patient exhales. The two vertically moving bars are distinguished by appropriate labels, as shown in FIG. 2 by the label "Target" 255 for the guide bar and the label "You" 245 for the bar showing the patient's current respiratory position.

The arrangement shown in FIG. 2 allows the minimum amount of necessary information to be displayed to the patient, maximizing their ability to follow the guide. When the patient synchronizes breathing with the guide, the top edge 228 of the biofeedback bar 240 will align with the top edge 258 of the guide bar 250, forming line segments 228 and 258 into segments of a common horizontal line. Departures from this alignment are readily apparent to the patient. Those skilled in the art will appreciate that this minimum amount of necessary information may be displayed in other ways without departing from the spirit of the invention. For example, the bars may be displayed so as to move horizontally, with an exhale limit appearing on the left side of the display and an inhale limit appearing on the right side of the display. Similarly, a polar coordinate system could be used for the display, with movement of the respective bars being in a semicircular arc, the respective line segments being segments of a radius that rotates from an exhale limit to an inhale limit.

This invention can be used for diagnostic imaging for thoracic and abdominal sites, as well as radiotherapy imaging and treatment to abdominal and thoracic sites.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A computer implemented method for respiratory audio-visual biofeedback for imaging and radiotherapy treatment, the computer performing steps comprising:

displaying by the computer for a patient a continuously changing target indication of the patient's respiratory position;

displaying by the computer for the patient a current indication of the patient's respiratory position; and aligning by the computer the target indication display and the current indication display so that a difference between the patient's current respiratory position and the patient's target respiratory position is readily apparent to the patient wherein the target indication, the current indication and the readily apparent difference are displayed continuously between an end-exhale position and an end-inhale position.

2. A method as in claim 1, wherein the patient's current respiratory position is indicated by a current marker along a current line from the end-exhale position to the end-inhale position and wherein the target respiratory position is indicated by a target marker along a target line from the end-exhale position to the end-inhale position, the lines for target respiratory position and current respiratory position being aligned in parallel in a first direction so that if the patient's current respiratory position is synchronized with the patient's target respiratory position the corresponding markers are aligned in a second direction perpendicular to the first direction.

3. A method as in claim 2, wherein the corresponding markers are straight line segments in said second direction.

4. A method as in claim 3, wherein each straight line segment is at one end of a bar, the bar extending along said first direction.

5. A method as in claim 4, wherein the bar measuring the patient's current respiratory position extends from the current line segment in the direction of the end-exhale position.

6. A method as in claim 5, wherein a target end-exhale limit and a target end in-hale limit are marked on the display.

7. A method as in claim 6, wherein the target end-exhale limit and the target end-inhale limit are marked by lines in said second direction.

8. A method as in claim 4, wherein the first direction is vertical and the second direction is horizontal, as the display is viewed by the patient.

9. In a computer implemented method for respiratory audio-visual biofeedback for imaging and radiotherapy treatment, said method displaying for a patient target end ex-hale and target end in-hale limits together with a current respiratory position to be kept within said limits by control of breathing by the patient, an improvement comprising:

displaying by the computer a continuously changing target respiratory position of the patient, the target position varying continuously in accordance with a pattern learned from the patient; and aligning by the computer the display of the target respiratory position and the display of the current respiratory position so that a difference between the patient's current respiratory position and the patient's target respiratory position is readily apparent to the patient wherein the target indication, the current indication and the readily apparent difference are displayed continuously between an end-exhale position and an end-inhale position.

10. An improvement as in claim 9, wherein the patient's current respiratory position and the patient's target respiratory position are shown by the vertical movement of parallel bars, a synchronization of current respiration with the target being shown by horizontal alignment of corresponding moving top portions of the respective parallel bars.

11. An improvement as in claim 9, wherein the target position is determined by an average of respiratory traces obtained by monitoring the patient.

12. An improvement as in claim 9, wherein the target position is determined by a mathematical algorithm falling within an envelope established by a plurality of respiratory traces obtained by monitoring the patient.

13. A display apparatus for respiratory audio-visual biofeedback, comprising:
   a target display of a patient's respiratory position, the target display showing a continuously varying target respiratory position over time in accordance with a pattern learned from the patient; and
   a display over time of the patient's current respiratory position,
   wherein the target display and the display of the patient's current respiratory position are aligned so that a difference between the patient's current respiratory position and the patient's target respiratory position is readily apparent to the patient,
   wherein the target respiratory position, the current respiratory position, and the readily apparent difference are displayed continuously between an end-exhale position and an end-inhale position.

14. A display apparatus as in claim 13, wherein the patient's current respiratory position is indicated by a current marker along a current line from an end-exhale position to an end-inhale position and wherein the target respiratory position is indicated by a target marker along a target line from the end-exhale position to the end-inhale position, the lines for target respiratory position and current respiratory position being aligned in parallel in a first direction so that if the patient's current respiratory position is synchronized with the patient's target respiratory position the corresponding markers are aligned in a second direction perpendicular to the first direction.

15. A display apparatus as in claim 14, wherein the corresponding markers are straight line segments in said second direction.

16. A display apparatus as in claim 15, wherein each straight line segment is at one end of a bar, the bar extending along said first direction.

17. A display apparatus as in claim 16, wherein the bar measuring the patient's current respiratory position extends from the current line segment in the direction of the end-exhale position.

18. A display apparatus as in claim 17, wherein a target end-exhale limit and a target end in-hale limit are marked on the display.

19. A display apparatus as in claim 18, wherein the target end-exhale limit and the target end-inhale limit are marked by lines in said second direction.

20. A display apparatus as in claim 16, wherein the first direction is vertical and the second direction is horizontal, as the display is viewed by the patient.

* * * * *